US005679331A

United States Patent [19]

Hague et al.

[11] Patent Number: 5,679,331
[45] Date of Patent: Oct. 21, 1997

[54] HAIR CONDITIONING COMPOSITION

[75] Inventors: Jonathan David Hague, Merseyside; Abid Nadim Khan-Lodhi, Cheshire; Euan Stuart Reid, Merseyside, all of United Kingdom

[73] Assignee: Chesebrough-Pond's USA Co., Division of Conopco, Inc., Greenwich, Conn.

[21] Appl. No.: 620,965

[22] Filed: Mar. 22, 1996

[30] Foreign Application Priority Data

Mar. 24, 1995 [GB] United Kingdom ............... 9506038

[51] Int. Cl.⁶ ................................................ A61K 7/075
[52] U.S. Cl. .................. 424/70.19; 424/70.28; 424/70.21; 424/70.24; 424/70.27; 424/70.31
[58] Field of Search ............... 424/70.19, 70.28, 424/70.21, 70.24, 70.27, 70.31

[56] References Cited

U.S. PATENT DOCUMENTS

| | | |
|---|---|---|
| 4,370,272 | 1/1983 | Wechsler et al. . |
| 4,744,977 | 5/1988 | Hensen et al. . |
| 4,874,554 | 10/1989 | Lange et al. . |
| 5,240,698 | 8/1993 | Traver et al. ............... 424/71 |
| 5,393,519 | 2/1995 | Dowell et al. .............. 434/70.11 |
| 5,505,866 | 4/1996 | Bacon et al. ............... 525/8.6 |

FOREIGN PATENT DOCUMENTS

| | | |
|---|---|---|
| 0 100 164 | 2/1984 | European Pat. Off. . |
| 0 252 441 | 1/1988 | European Pat. Off. . |
| 0 309 052 | 3/1989 | European Pat. Off. . |
| 0 345 842 | 12/1989 | European Pat. Off. . |
| 0 571 086 | 11/1993 | European Pat. Off. . |
| 0 636 356 | 2/1995 | European Pat. Off. . |
| 2430140 | 2/1976 | Germany . |
| 4138630 | 5/1993 | Germany . |
| 52-122638 | 10/1977 | Japan . |

Primary Examiner—Thurman K. Page
Assistant Examiner—D. Faulkner
Attorney, Agent, or Firm—Milton L. Honig

[57] ABSTRACT

A transparent conditioning composition for hair comprises a stable transparent dispersion of: (i) a substantially water-insoluble quaternary ammonium material having two $C_{12-28}$ alkyl or alkenyl groups connected to the quaternary ammonium head group via at least one ester linkage, and (ii) a solubilising agent comprising at least one surfactant, preferably cationic surfactants.

8 Claims, No Drawings

HAIR CONDITIONING COMPOSITION

TECHNICAL FIELD

This invention relates to hair conditioning compositions, more particularly to hair conditioning compositions which are transparent.

BACKGROUND AND PRIOR ART

Hair conditioning compositions may be formulated to select those components which together impart a desirable combination of properties. Typically such compositions contain a mixture of substantially water-insoluble hydrocarbon-based conditioning agents, examples being fatty alcohols and acids, long chain dialkyl quaternary ammonium salts, fatty tertiary amine salts, paraffin waxes and glycerol fatty acid esters, dispersed in water, often also in the presence of a water-soluble long chain cationic surfactant. The total solids content of such products is usually between 3 and 10%, and the conditioning agents generally form a mixed morphology comprising a dispersion of stacked lamellar structures and solid fatty particles.

Compositions of the type described above offer very effective detangling of wet hair, and impart other desirable properties to hair such as ease of dry combing, smoothness both wet and dry, softness in the dry state, and lack of flyaway due to reduction of the static charge generated on hair. This combination of properties is generated to a greater degree by the molecular organisation of components in the lamellar structures.

Such compositions are, however, invariably opaque since both the lamellar structures and fatty particles are present at the super-micron size range, and so scatter light very effectively. However, hair conditioning compositions are often desired to be transparent, i.e. optically clear or substantially clear. This is of benefit as regards visual product appeal to the consumer.

For people whose hair is naturally greasy, conventional opaque conditioners are also often undesirable because of heavy coating and residue build up on the hair and excessive conditioning perceptions. It is believed that excessive levels of hydrocarbon-based conditioning agents in conditioning compositions contribute to the sensory negatives of heaviness and greasiness.

There is thus a desire to provide a transparent conditioning composition which is lower in its levels of substantially insoluble hydrocarbon based conditioning agents, so minimising the problems associated with high levels of fatty material. There is equally the requirement, however, to ensure that performance attributes of the composition in terms of the desirable hair conditioning properties referred to above are not reduced as a consequence.

One particular known hair conditioning composition which is transparent is disclosed in JP-A-52-122638 and comprises a cationic surfactant component, particularly cetyltrimethylammonium chloride, and a phosphoric acid ester component, particularly mono/diphosphate ester of C18 (3EO) alcohol. However, such compositions have been recognised as having limited hair conditioning properties. It has also been found that it is not possible to simply increase the proportion of phosphoric acid ester component with the aim of enhancing the hair conditioning benefits imparted by the composition, since that results in a cloudy product, which, as discussed, is undesirable. EP-A-0100164 discloses hair conditioning preparations comprising anionic surfactant and a cationic polymer, rendered clear by inclusion of a clarifying agent. When diluted with water upon use, an insoluble complex is formed between the cationic polymer and anionic surfactant, which is precipitated and thereby deposited on the hair. Such preparations typically deposit material very heavily onto the hair, which can lead to dulling effects and greasy build-up.

U.S. Pat. No. 4,744,977 discloses hair conditioning compositions comprising particular β-hydroxy quaternary ammonium compounds. These hair conditioning compounds are indicated as being more compatible with high-foam anionic surfactants compared with other known quaternary ammonium compounds, giving products which are less cloudy and less prone to precipitation of insoluble deposits. The reference discloses generally a wide variety of anionic surfactants for use in combination with the defined cationic surfactant in hair conditioning shampoos.

EP-A-571086 discloses hair care compositions comprising an ester-linked quaternary ammonium compound, and possibly also a cationic surfactant as a conditioning agent. There is no disclosure of a transparent dispersion of such materials.

EP-A-345842 discloses a fabric softener comprising a quaternized ester-ammonium compound and a substituted imidazoline ester in the form of sub-micron size dispersions in liquid carrier. Optional ingredients include surfactants. There is no disclosure of a hair conditioner in the form of a transparent dispersion.

EP-A-309052 discloses a fabric softener comprising a quaternized ester-amine and a linear alkoxylated alcohol in the form of a sub-micron size dispersion in liquid carrier. Optional surfactant may be included. There is no disclosure of a hair conditioner in the form of a transparent dispersion.

U.S. Pat. No. 4,370,272 discloses novel quaternary ammonium compounds useful, inter alia, in hair conditioners. There is no disclosure of a hair conditioner in the form of a transparent dispersion.

We have now found that hair conditioning compositions can be prepared which are optically clear or transparent without the need for inclusion of clarifying agents, transparency materials or heavily-flocculating polymer-surfactant mixtures. The present invention can provide hair conditioning compositions having excellent optical properties, despite containing principally water-insoluble hair conditioning agents, and which furthermore deposit/build up perceivably less material to the hair surface relative to conventional opaque conditioners, but with no concurrent loss of desired conditioning performance.

SUMMARY OF THE INVENTION

According to one aspect of the invention there is provided a hair conditioning composition comprising a transparent dispersion of:

(i) a hair conditioning compound comprising a substantially water-insoluble quaternary ammonium material having two $C_{12-28}$ alkyl or alkenyl groups connected to the quaternary ammonium head group via at least one ester linkage, and;

(ii) a solubilising agent comprising at least one surfactant selected from anionic, amphoteric, nonionic, and cationic surfactants or mixtures thereof.

DETAILED DESCRIPTION OF THE INVENTION

Without wishing to be bound by theory it is believed that the hair conditioning composition of the invention is not in conventional lamellar form, and in water may be solubilised at least partially by the action of the surfactant to form self-size-limiting molecular aggregates, such as micelles or micellar solutions with solid or liquid interiors or mixtures thereof. These can be considered as particles dispersed in a continuous phase. The aggregates have a predictable small particle size (less than 0.1 micron) which is not affected by processing, resulting in production of an aqueous dispersion that is transparent and also has good hair conditioning properties. It is thought that it is this new structure of the hair conditioning compositions of the invention that overcomes the problems of the prior art.

The dispersion is generally an aqueous dispersion.

When the hair conditioning composition is formulated with water to a concentration of 1 wt % of the hair conditioning compound (i), the compound (i) is substantially present in solution, that is, at least about 70 wt % and preferably 80 wt % of compound (i) is in solution.

The transparent dispersion is found to be stable over an extended period of time, of many months at least, so that the compositions of the invention have a reasonable shelf life.

THE HAIR CONDITIONING COMPOUND

The hair conditioning compounds used in the compositions of the invention are molecules which provide excellent hair conditioning, characterised by chain melting—L$\beta$ to L$\alpha$—transition temperature greater than 25° C., preferably greater than 35° C., most preferably greater than 45° C. This L$\beta$ to L$\alpha$ transition can be measured by DSC as defined in "Handbook of Lipid Bilayers", D. Marsh, CRC Press, Boca Raton Fla., 1990 (Pages 137 and 337).

Substantially insoluble hair conditioning compounds in the context of this invention are defined as hair conditioning compounds having a solubility less than $1 \times 10^{-3}$ wt % in demineralised water at 20° C. Preferably the hair conditioning compounds have a solubility less than $1 \times 10^{-4}$. Most preferably the hair conditioning compounds have a solubility at 20° C. in demineralised water from $1 \times 10^{-8}$ to $1 \times 10^{-6}$. However, when solubilised by the action of the solubilising agent, the hair condition compounds can form a transparent, small particle size dispersion.

It is preferred if the alkyl or alkenyl groups of the hair conditioning compound are predominantly linear.

Preferably the hair conditioning compound of the invention has two long chain alkyl or alkenyl chains with an average chain length equal to or greater than $C_{14}$. More preferably each chain has an average chain length equal to or greater than $C_{16}$. Most preferably at least 50% of each long chain alkyl or alkenyl group have a chain length of $C_{18}$.

It is preferred if the hair conditioning compound is a water insoluble quaternary ammonium material which comprises a compound having two $C_{12-18}$ alkyl or alkenyl groups connected to the molecule via at least one ester link. It is more preferred if the quaternary ammonium material has two ester links present.

A preferred ester-linked quaternary ammonium material for use in the invention can be represented by the formula:

$$R^1-\underset{\underset{(CH_2)_n-T-R^2}{|}}{\overset{\overset{R^1}{|}}{N^+}}-(CH_2)_n-T-R^2$$

wherein each $R^1$ group is independently selected from $C_{1-4}$ alkyl, hydroxyalkyl or $C_{2-4}$ alkenyl groups; and wherein each $R^2$ group is independently selected from $C_{8-28}$ alkyl or alkenyl groups;

each T independently represents

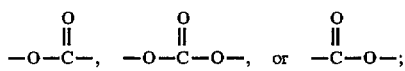

and n is an integer from 0 to about 5.

An especially preferred type of quaternary ammonium material can be represented by the formula:

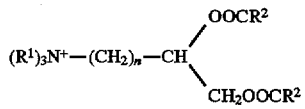

wherein $R^1$, n and $R^2$ are as defined above.

It is advantageous for environmental reasons if the quaternary ammonium material is biologically degradable.

Compounds of this formula suitable for use in the hair conditioning compositions of the invention and their method of preparation are, for example, described in U.S. Pat. No. 4,137,180 (Lever Brothers), the disclosure of which is incorporated herein by reference.

A particularly preferred example is 1,2-ditallowoyloxy-3-trimethylammonium propane chloride.

The amount of the hair conditioning compound in the composition of the invention is suitably in the range of from about 0.01 to about 20 wt % based on total weight of the composition, more preferably from 0.05 to 10 wt %, even more preferably from 1 to 2 wt %. It is generally preferred not to use more than 2% of the hair conditioning compound, as higher concentrations may adversely affect turbidity.

THE SOLUBILISING AGENT

The solubilising agent comprises at least one surfactant selected from anionic, amphoteric, nonionic, and cationic surfactants or mixtures thereof.

These may be characterised in terms of their phase behaviour. Suitable solubilising agents are surfactants for which, when contacted with water, the first lyotropic liquid crystalline phase formed is normal cubic (I1) or normal cubic-bicontinuous (V1) or hexagonal (H1) or nematic (Ne1), or intermediate (Int1) phase as defined in the article by G J T Tiddy et al, J Chem Soc. Faraday Trans. 1., 79, 975, 1983 and G J T Tiddy, "Modern Trends of Colloid Science in Chemistry and Biology", Ed. H-F Eicke, 1985 Birkhauser Verlag Basel. Surfactants forming L$\alpha$ phases at concentrations of less than 20 wt % are less suitable.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule. Examples include sodium lauryl sulphate, triethanolamine lauryl sulphate 1EO, 2EO and 3EO, ammonium lauryl sulphate and ammonium lauryl ether sulphate 1EO, 2EO and 3EO.

Suitable amphoteric surfactants include alkyl amine oxides, alkyl phosphine oxides, alkyl sulphoxides, alkyl betaines, alkyl amidopropyl betaines, alkyl sulphobetaines, alkyl glycinates, alkylcarboxyglycinates, alkyl amphopropionates, alkyl amphoglycinates, alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

Nonionic surfactants include condensation products of aliphatic ($C_{8-18}$) primary or secondary linear or branched-chain alcohols or phenols with alkylene oxides, usually ethylene oxide, and generally having from 6 to 30 ethylene oxide groups.

Other suitable nonionics include mono- or di-alkyl alkanolamides. Examples include coco mono- or di-ethanolamide and coco mono-isopropoanolamide.

Further suitable nonionic surfactants are the alkyl polyglycosides (APGs). Typically the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues or mixtures of $C_5$ and $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as ORAMIX NS10 ex Seppic; PLANTAREN 1200 and PLANTAREN 2000 ex Henkel.

Silicone-based nonionic or cationic surfactants such as DC 190 ex Dow Corning (nonionic) may also be used.

Cationic surfactants are particularly preferred solubilising agents according to the invention.

Preferred types of cationic surfactants for use in the invention are quaternary ammonium hydroxides or salts thereof, e.g. halides. Examples of suitable cationic surfactants for use in the invention include:

tetramethylammonium salts, tetraethylammonium salts, cetyltrimethylammonium salts, cetylpyridinium chloride, octyltrimethylammonium salts, dodecyltrimethylammonium salts, hexadecyltrimethylammonium salts, octyldimethylbenzylammonium salts, decyldimethylbenzylammonium salts, stearyldimethylbenzylammonium salts, oleyldimethylbenzylammonium halides, methyl bis-(-2-hydroxyethyl) oleyl ammonium chloride, oleyl ammonium chloride, tallow trimethylammonium salts, cocotrimethylammonium salts and polyethoxylated quaternary ammonium salts. Preferred ammonium salts are the chlorides and bromides.

Further suitable cationic surfactants include those identified by the CTFA definitions Quaternium-5, Quaternium-31, Quaternium-18, and salts, eg chloride, of the quaternary ammonium derivative of formula:

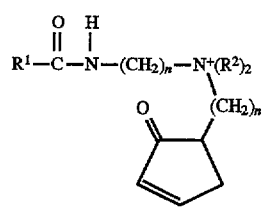

in which $R^1$ represents $C_{12-22}$ alkyl, preferably $C_{18}$ alkyl, each $R^2$ independently represents $C_{1-4}$ alkyl, and n is an integer from 1 to about 5.

Other surfactants which under appropriate pH conditions have cationic character can also be used, for example amidoamine derivatives of lauric acid and alkyl betaines.

Mixtures of any of the foregoing materials may also be suitable. A particularly preferred cationic surfactant for use in the invention is cetyltrimethylammonium chloride (CTAC), which is available commercially for example as ARQUAD 16–50 ex Akzo.

The solubilising agent may optionally further comprise a non-surfactant co-solubiliser. Preferred co-solubilisers include polyethylene glycols (PEG) having a molecular weight ranging from 200–6000, most preferably from 1000–2000, urea, acid amides up to and including chain lengths of $C_6$, citric acid and other polycarboxylic acids as disclosed in EP 0 404 471 (Unilever), glycerol, sorbitol, and sucrose. Particularly preferred is propylene glycol.

It is advantageous if the weight ratio of solubilising agent (excluding any co-solubiliser present) to hair conditioning compound is in the range of from 1:50 to 1:1, preferably from 1:20 to 1:2, most preferably from 1:10 to 1:5.

It is beneficial if the solubilising agent is present at a level greater than about 0.1 wt % of the total composition, such as between 0.1 and 2 wt %, eg between 0.2 and 0.5 wt %.

The currently preferred combination of conditioning compound and solubilising agent is 1,2-ditallowoyloxy-3-trimethylammonium propane chloride (HEQ), conveniently in an amount in the range 1 to 2 wt %, as conditioning compound, and CTAC, conveniently in an amount of about 0.2 wt %, as solubilising agent. Good results have also been obtained by replacing HEQ with dihardened tallow ethyl ester dimethyl ammonium chloride (DEEDMAC), which is available commercially for example as GENAMIN EQ ex Hoechst.

OTHER INGREDIENTS

The hair conditioning compositions of the present invention may contain additional components usually found in hair care compositions.

For instance, the hair conditioning compositions of the invention may contain a suitable amount of a thickening agent such as a polymeric thickener, such as hydroxyethyl cellulose (available commercially as NATROSOL).

One optional component which may be included in the hair conditioning compositions of the invention is a fatty alcohol or fatty acid, or derivative thereof, or a mixture of any of these, having a chain length of from about 8 to about 28 carbon atoms, more preferably from about 12 to about 18 carbon atoms. These materials may be predominantly linear or may be branched.

Such fatty materials may be present in the compositions of the invention in a total amount of from about 0.001 to about 10 wt %, more preferably 0.01 to 5 wt %, e.g. 0.1 to 1 wt % based on the total weight of the composition.

The compositions of the invention may also optionally contain one or more additional conditioning agents. Suitable additional conditioning agents include cationic polymers, volatile or non-volatile silicones, quaternised silicones (e.g. those materials available under the trade name ABILQUAT ex Goldschmidt), perfluoropolyethers (eg those materials available under the trade name FOMBLIN ex Montefluos), protein hydrolysates, quaternised protein hydrolysates and other materials which are known in the art as having desirable hair conditioning properties.

Additional conditioning agents which are especially suitable include volatile or non-volatile silicone oils, such as for example polyalkylsiloxanes, polyalkylaryl siloxanes, silicone gums, cyclomethicones and aminofunctional silicones. Preferably these silicone materials are incorporated in the compositions as small droplets, preferably of droplet size smaller than 0.1 microns, more preferably smaller than 0.1 microns, most preferably smaller than 0.035 microns. The preferred level of additional conditioning agent(s), if present, in compositions of the invention is up to about 20 wt %, for example from 0.01 to 10 wt %, more preferably from 0.1 to 5 wt % based on the total weight of the composition.

Other optional components which may be present in the hair conditioning compositions of the invention in addition to water include perfumes, colouring agents, anti-bacterial agents, anti-dandruff agents, preservatives, proteins, polymers, sunscreens, buffering agents, polyols and other moisturising agents, and natural ingredients such as herb and other plant extracts.

The hair conditioning compositions of the invention preferably comprise from 20 to 99.5 wt % of water based on the total weight of the composition, preferably 60 to 98 wt %, most preferably 75 to 98 wt %, so that the composition is in the form of a transparent aqueous dispersion.

The composition is conveniently made by agitating a mixture of the hair conditioning compound, solubilising agent and water at a temperature at or above the gel-lamellar phase transition temperature for a suitable time until the formulation becomes transparent, and then adding any further ingredients. For compositions comprising HEQ and CTAC the gel-lamellar phase transition temperature is in the range 45° C. to 50° C., and agitation for about 30 minutes at this temperature is appropriate.

The hair conditioning compositions of the invention are intended particularly for post-wash use. The composition is applied to wet hair after washing in a suitable amount, eg in the range 5 to 10 grams/head, left for about a minute and then rinsed off.

The invention is further illustrated by way of the following non-limitative examples. In the examples all percentages are expressed by weight. Examples of the invention are designated by numbers, whereas Comparative Examples are designated by letters.

EXAMPLES

Examples 1 and 2

Hair conditioning preparations were prepared containing the following ingredients in the amounts shown below in Table 1.

TABLE 1

| INGREDIENT | Example 1 | Example 2 | A |
|---|---|---|---|
| HEQ[1] | 1.0 | 2.0 | 1.0 |
| CTAC[2] | 0.2 | 0.2 | — |
| Natrosol[3] | 1.2 | 1.2 | 1.2 |
| Propylene Glycol | 5.0 | 5.0 | 5.0 |

TABLE 1-continued

| INGREDIENT | Example 1 | Example 2 | A |
|---|---|---|---|
| (99%) | | | |
| Formaldehyde (30%) | 0.1 | 0.1 | 0.1 |
| Perfume | 0.15 | 0.15 | 0.15 |
| Demineralised water | | to 100 | |

[1] 1,2-ditallowoyloxy-3-trimethylammonium propane chloride (90% purity).
[2] Cetyl trimethyl ammonium chloride, as ARQUAD 16-50 ex Akzo (cationic surfactant).
[3] Hydroxyethyl cellulose Examples 1 and 2 were prepared by adding water to the CTAC and HEQ, heating to 45° C., and stirring at that temperature for about 30 minutes. Once clear, the other formulation ingredients were incorporated at 40°–45° C.

Comparative Example A was prepared by dissolving HEQ alone in propylene glycol, dispersing the solvent/solid mixture in water at 85° C. by fast vortex, and adding the other formulation ingredients during cooling.

Visual Attributes

Clarity of the formulations after mixing was assessed by eye, and the results are given below in Table 2.

TABLE 2

| EXAMPLE | APPEARANCE |
|---|---|
| 1 | Good clarity with Natrosol and perfume Stable to particle growth/precipitation |
| 2 | Good clarity with Natrosol and perfume Stable to particle growth/precipitation |
| A | Cloudy. Will not solubilise perfume |

The results show that dispersions of HEQ without CTAC (Comparative Example A) are cloudy. Addition of CTAC, however, (Examples 1 and 2) remedies the problem of cloudiness and allows perfume to be added without inducing cloudiness in the final formulation. Examples 1 and 2 thus result transparent dispersions, having a particle size of less than 0.1 micron. The dispersions of Examples 1 and 2 are stable, and remain transparent, over an extended period of time, of many months.

Wet Combing Performance

The hair conditioning compositions of Examples 1 and 2 were tested against a currently marketed transparent conditioner (Comparative Example B) having the formulation shown below in Table 3:

TABLE 3

| Ingredient | % |
|---|---|
| Natrosol | 1.1 |
| Merquat 100 (60%)[4] | 1.25 |
| Amonyl 380BAU[5] | 2.0 |
| Cremaphore RH410[6] | 0.6 |
| Sodium chloride | 1.0 |
| Perfume | 0.3 |
| Minor ingredients & water | to 100 |

[4] Polyquaternium-6 (ex Croxton and Garry)
[5] Cocamidopropyl betaine (30%, ex Seppic)
[6] PEG 40 Hydrogenated Castor Oil (ex BASF)

Table 4 displays a summary of automated wet combing force measurements which provide % reductions in combing force due to conditioner application. Rinse-off conditioner protocols were used in each case.

TABLE 4

| Example | % Reduction in Combing Force |
|---|---|
| 1 | 58 |
| 2 | 60 |
| B | 30 |

It can be seen that the Examples of the invention offer a significant improvement in wet combing force reduction over Comparative Example B.

Salon Test

The formulation of Example 2 was salon tested in a paired comparison test against a currently marketed opaque conditioner (Comparative Example C) having the formulation shown below in Table 5:

TABLE 5

| Ingredient | % |
|---|---|
| CTAC | 2.1 |
| Cetearyl alcohol | 3.0 |
| Paraffin wax | 1.0 |
| Glyceryl stearate | 0.7 |
| Formaldehyde (30%) | 0.15 |
| Perfume | 0.4 |
| Minor ingredients and water | to 100 |

Various conditioner attributes were hairdresser assessed, and 36 panellists were employed for each comparison. The test protocol used was a 3 g dosage each of the respective formulations each per ½ head in post-wash treatment of wet hair.

The results are shown below in Table 6.

TABLE 6

| Conditioner Attribute | Assessment of Preference |
|---|---|
| Smooth feel | Equal preference for each formulation |
| Slippery feel | Comparative Example C preferred |
| Ease of wet combing | Example 2 preferred |
| Ease of detangling | Equal preference for each formulation |
| Gloss | Equal preference for each formulation |

It can be seen that the formulation of the Example of the invention achieves parity with the formulation of the Comparative Example on all main conditioning attributes despite the Comparative Example's higher proportion of fatty material.

Examples 3 and 4

Effect of Silicone

Hair conditioning preparations were prepared by the method given for Examples 1 and 2 and containing the following ingredients in the amounts shown below in Table 7.

TABLE 7

| | Example | |
|---|---|---|
| Ingredient | 3 | 4 |
| HEQ | 1.0 | 1.0 |
| CTAC | 0.5 | 0.5 |
| DC2 - 1685[a] | — | 2.0 |
| Natrosol | 1.2 | 1.2 |
| Propylene Glycol (99%) | 5.0 | 5.0 |
| Formaldehyde (30%) | 0.1 | 0.1 |
| Perfume | 0.15 | 0.15 |
| Demineralised water | to 100 | |

[a]Silicone microemulsion ex Dow Corning (Dimethiconol (25%) + Laureth-23 (6%) + TEA dodecylbenzene sulfonate (15%))

Table 8 displays wet combing results for Examples 3 and 4.

TABLE 8

| Example | % Reduction in Combing Force |
|---|---|
| 3 | 62 |
| 4 | 72 |

It can be seen that inclusion of silicone boosts the wet conditioning attributes of the formulation.

We claim:

1. A hair conditioning composition comprising a transparent dispersion of:
   (i) a hair conditioning compound comprising a substantially water-insoluble quaternary ammonium material having two $C_{12-28}$ alkyl or alkenyl groups connected to the quaternary ammonium head group via at least one ester linkage, and;
   (ii) a solubilising agent comprising cetyl trimethylammonium chloride.

2. A hair conditioning composition according to claim 1, in which the weight ratio of solubilising agent to hair conditioning compound is in the range of from 1:50 to 1:1.

3. A hair conditioning composition according to claim 2, in which the ratio of solubilising agent to hair conditioning compound is within the range of from 1:10 to 1:5.

4. A hair conditioning composition according to claim 1, in which the hair conditioning compound is 1,2-ditallowoyloxy-3-trimethylammonium propane chloride.

5. A hair conditioning composition according to claim 1, in which the hair conditioning compound is present in an amount in the range 0.01 to 20 wt %.

6. A hair conditioning composition according to claim 1, in which the solubilising agent is present in an amount in the range 0.1 to 2 wt %.

7. A hair conditioning composition according to claim 1, which further comprises a volatile or non-volatile silicone.

8. A hair conditioning composition according to claim 1, in which the composition is in the form of self-size-limiting molecular aggregates.

* * * * *